United States Patent [19]

Hardy

[11] 3,931,103
[45] Jan. 6, 1976

[54] COPPER INHIBITORS FOR POLYOLEFINS

[75] Inventor: William Baptist Hardy, Bound Brook, N.J.

[73] Assignee: American Cyanamid Company, Stamford, Conn.

[22] Filed: Oct. 18, 1974

[21] Appl. No.: 515,941

[52] U.S. Cl.... 260/45.85 B; 252/404; 260/45.9 NC; 260/45.95 R; 260/45.95 H; 260/559
[51] Int. Cl.² ................................................ C08G 6/00
[58] Field of Search ............ 260/45.85 B, 45.95 H, 45.95 R, 260/45.9 NC; 252/404

[56] References Cited
UNITED STATES PATENTS

| | | | |
|---|---|---|---|
| 3,734,885 | 5/1973 | Muller et al. | 260/45.9 |
| 3,849,492 | 11/1974 | Brunetti | 260/45.9 |

*Primary Examiner*—V. P. Hoke
*Attorney, Agent, or Firm*—Philip Mintz

[57] ABSTRACT

Compounds of the formula

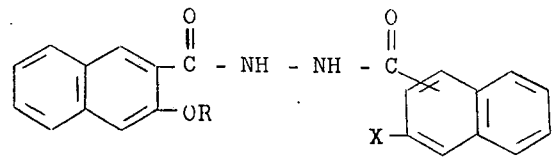

wherein R is an alkyl of 1 to 8 carbon atoms and X is hydrogen or —OR, are useful, in combination with hindered-phenol antioxidants, for inhibiting thermal degradation of polyolefins, especially polypropylene, in contact with copper as metal, alloys, oxides, or salts. Such compounds can be prepared by reacting hydrazine with a naphthoic acid ester which may have an alkoxy group in the 3- position to form an intermediate which reacts with 3-alkoxy-2-naphthoyl chloride to form said compounds.

13 Claims, No Drawings

COPPER INHIBITORS FOR POLYOLEFINS

This invention relates to the stabilization of polyolefins, especially those wherein the polyolefin chain contains a plurality of tertiary carbon atoms or branch points, such as polypropylene and polybutene-1, against degradation when in contact with copper, copper alloys, copper oxides, or copper salts. It also relates to certain novel compounds, useful in combination with hindered-phenol antioxidants for such stabilization.

It is well known that polyolefins are subject to degradation caused by heat, ultraviolet light, and oxygen and that many materials have been found to inhibit such degradation, such as antioxidants and ultraviolet absorbers. It is also well known that copper, whether in the form of copper metal, copper alloys, copper oxides, or copper salts, catalyzes or otherwise greatly increases the susceptibility of polyolefins to degradation on exposure to heat, as described in Hansen et al., J. Poly Sci., Part A, vol. 2, pp. 587–609 (1964), Hansen et al., Poly Eng. & Sci., vol. 5, October 1965, pp. 223–226, as well as in U.S. Pat. Nos. 3,440,210; 3,462,517; and 3,549,572. Other transition metals also catalyze the heat degradation of polyolefins similarly. Each of these references, and U.S. Pat. Nos. 3,110,696; 3,117,104; 3,660,438; German Pat. Nos. 2,124,641; 2,140,350; and Belgian Pat. No. 773,596, mention various classes of compounds which they either knew of or discovered as useful for inhibiting copper-catalyzed thermal degradation of polyolefins. The general class of hindered-phenol antioxidants normally used to provide protection to polyolefins against degradation by oxygen fails to provide adequate protection against copper-catalyzed degradation (Hansen et al., supra, and U.S. Pat. No. 3,549,572 col. 1, line 65 through col. 2, line 12 indicate that the presence of the antioxidant actually makes the copper-catalyzed degradation worse than its absence!) although they have been used in combination with some of the copper inhibitor compounds to provide enhanced protection. However, none of these compounds has proven to be completely satisfactory and the problem still awaits a satisfactory solution. Also, as pointed out in Hansen et al., page 594 bottom, predictability in this area is very poor since compounds similar to useful inhibitors were frequently useless. As a result, the use of polyolefins in contact with copper or other transition metals, as for insulation on copper wire for instance, has been limited.

In accordance with the present invention, it has been discovered that compounds of the formula

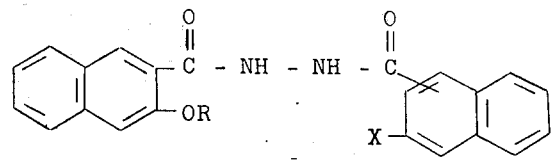

wherein R is an alkyl of 1 to 8 carbon atoms and X is hydrogen or —OR, are effective to inhibit copper or other transition-metal catalyzed degradation of polyolefins, particularly those having a plurality of tertiary carbon atoms or branch points, such as polypropylene, when used in combination with hindered-phenol antioxidants.

These compounds can readily be prepared by various sequences of conventional organic reactions. For example, they can be prepared by reacting 3-alkoxy-2-naphthoyl chloride (prepared by reacting thionyl chloride with 3-alkoxy-2-naphthoic acid) with the appropriate naphthoylhydrazine (e.g. 3-alkoxy-2-naphthoylhydrazine made by reacting methyl 3-alkoxy-2-naphthoate with hydrazine or α- or β-naphthoylhydrazine by reacting ethyl α- or β-naphthoate with hydrazine). This complete reaction sequence can be illustrated as follows:

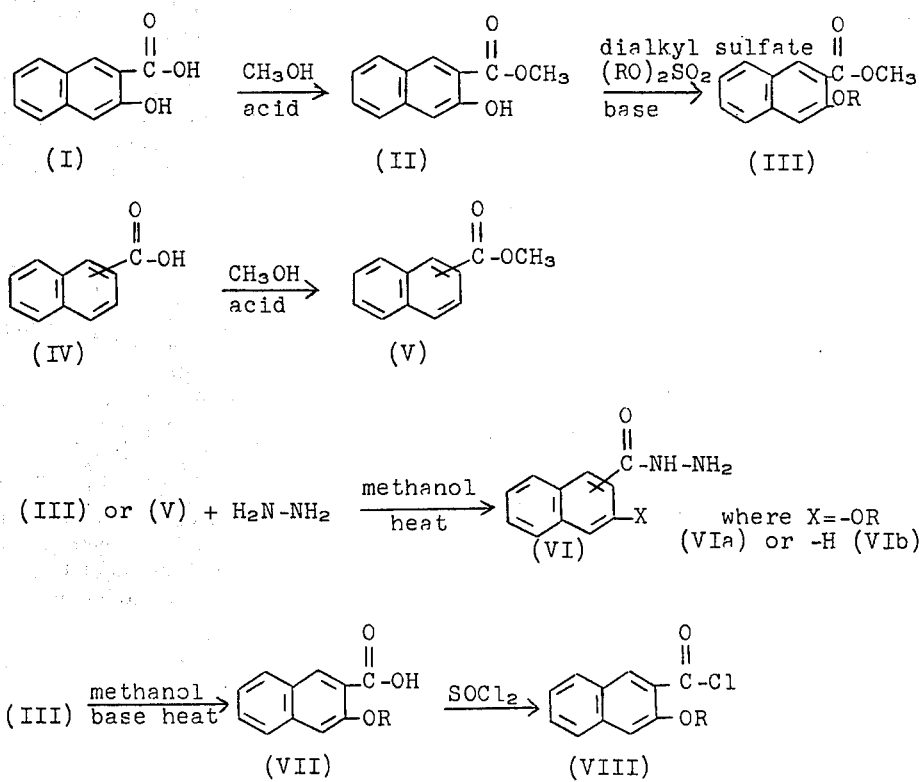

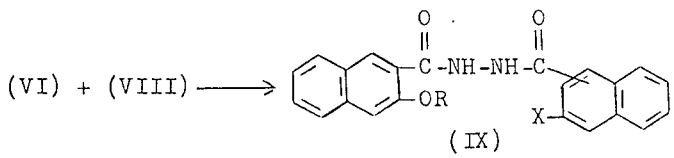

$$(VI) + (VIII) \longrightarrow (IX)$$

It will be understood that these compounds (compound IX) may additionally be substituted on the naphthalene moieties, particularly on the rings remote from the bis(carbonyl)hydrazine bridge with inert substituents which do not interfere with the ability of these compounds to function as copper inhibitors, such as lower alkyl or halogen groups. Howeever, for reasons of economy, it is generally preferred that no additional substituents be present in these compounds.

For effective stabilization of polyolefins against copper-catalyzed degradation, these compounds should be used in combination with a hindered-phenol antioxidant. Many hindered-phenol antioxidants are well known and are conventionally used in polyolefins. Illustrative of these hindered-phenol antioxidants are 6,6'-di-t-butyl-4,4'-bis-o-cresol; 4,4'-methylene-bis(3-methyl-6-t-butylphenol); 2,6-di-t-butyl-4-methylphenol; 2,2'-thiobis(4-methyl-6-t-butylphenol); 4,4'-thiobis(3-methyl-6-t-butylphenol); 2,2'-methylenebis(4-ethyl-6-t-butylphenol); the benzyl esters of β-(subst. hydroxyphenyl)propionic acids described in U.S. Pat. No. 3,649,667; tris(3,5-di-t-butyl-4-hydroxybenzyl)isocyanurate of U.S. Pat. Nos. 3,531,483 and 3,637,582; bis-, tris-, and tetrakis-(4-t-butyl-3-hydroxy-2,6-dimethylbenzyl) thiolesters of U.S. Pat. No. 3,810,929; 2,4,6-trialkyl-3-(higher alkyl-thiomethylene)-phenols of U.S. Pat. No. 3,660,352; 1,3,4-thiadiazole-bridged bis-thiomethylene-2,4,6-trialkylphenols of U.S. Pat. No. 3,676,449; pentaerythrityl tetrakis-3-(3,5-di-t-butyl-4-hydroxyphenyl) propionate of U.S. Pat. No. 3,285,855, sold as Irganox 1010; and the like.

In general, these compounds and the hindered-phenol antioxidants are used at total concentrations of about 0.01 to about 10% by weight of polyolefin, and preferably within the range of 0.05 to 3% by weight. The hindered-phenol antioxidant is used in an amount sufficient to stabilize the polyolefin against thermal degradation in the absence of copper, as is described in the foregoing references thereto. The hydrazine compound is used in an amount sufficient to reduce the effect of copper on such thermal degradation in the presence of the hindered-phenol antioxidant. Usually about equal amounts of each are used although this combination can be used in a weight ratio of 10:1 to 1:10 depending on the use to which the polyolefin is to be put and the environment to which it is to be exposed. The polyolefin composition stabilized by this stabilizer combination may also contain other additives, such as dyes, foaming agents, plasticizers, pigments, etc. as is conventional practice.

The following examples illustrate some especially preferred embodiments of this invention.

EXAMPLE 1

To 50 grams of 3-hydroxy-2-naphthoic acid (I) which was slurried in 200 milliliters of methanol, 10 milliliters of concentrated sulfuric acid was added and the reaction mixture was stirred at reflux for 4 hours, cooled, diluted with water, and the resulting solids filtered and dried in vacuo. There was obtained 53.25 grams of a yellow solid (99% yield) which was recrystallized from hexane to give 50.1 grams of pure methyl 3-hydroxy-2-naphthoate (II).

While stirring 24.5 grams of (II) and 16.5 grams of dimethyl sulfate in 100 milliliters of methanol at 0°–5°C., 7.5 grams of potassium hydroxide in 25 milliliters of methanol was added dropwise, and the reaction mixture was stirred for 12–15 hours at room temperature. The mixture was evaporated in vacuo and the residue was mixed with water and extracted with ether. The ether extract was washed several times with 5% potassium hydroxide solution and evaporated in vacuo to give 15.4 grams of a yellow oil, which was identified by infrared spectroscopy as methyl 3-methoxy-2-naphthoate (III).

To 15.4 grams of (III) dissolved in 50 milliliters of methanol, 4.5 grams of potassium hydroxide pellets were added and the reaction mixture was heated at reflux for 3 hours, then cooled, diluted with water, and extracted with ether to remove oily fractions. The aqueous solution was acidified with dilute sulfuric acid and the product was filtered, washed with water, and dried to give 12.16 grams of a pale yellow solid, 3-methoxy-2-naphthoic acid (VII) melting at 132°–133°C. Recrystallization from methanol gave 9.76 grams of pale yellow crystals of (VII) melting at 132.5°–134.1°C.

To 4.55 grams of (VII) slurried in 25 milliliters of benzene, 3.57 grams of thionyl chloride was added. The mixture was refluxed for several hours and the solvent was removed to yield a thick yellow resinous product, 3-methoxy-2-naphthoyl chloride (VIII).

EXAMPLE 2

To 13.9 grams of (III) was added 25 milliliters of methanol and 3.2 grams of anhydrous hydrazine. The reaction mixture was stirred at reflux for 6 hours and the solvent removed, leaving a solid which was filtered, washed with water, and dried to give 12.7 grams of solid product melting at 115°–120°C. Recrystallization of this solid from benzene twice gave 9.6 grams of beige platelets of 3-methoxy-2-naphthoylhydrazide (VIa) melting at 121.5°–123.5°C.

To a solution of 4.9 grams of (VIa) in 30 milliliters of warm pyridine was added a solution of (VIII) in 25 milliliters of tetrahydrofuran and the reaction mixture was stirred for about 15 minutes and diluted with water. The solid product was filtered, washed with water, methanol, and ligroin to give 6.9 grams of a beige solid. Recrystallization from glycol diacetate gave 6.5 grams of tan platelets of N,N'-bis(3-methoxy-2-naphthoyl)hydrazine (IXa) melting at 260.5°–263°C.

EXAMPLE 3

To 93 grams of ethyl 2-naphthoate was added 300 milliliters absolute ethanol and 125 grams anhydrous hydrazine. The reaction mixture was refluxed for about 16 hours, cooled to room temperature, and the white crystals which formed were filtered. Recrystallization from ethanol (300 milliliters) gave 78 grams of pale yellow crystals of 2-naphthoylhydrazine (VIb) melting at 145°–147°C.

To a slurry of 1.90 grams of (VIb) in 10 milliliters of dry pyridine was added a solution of 2.20 grams of (VIII) in 5–10 milliliters of tetrahydrofuran. The reaction mixture was allowed to stand for about 1 hour, was diluted with water, the precipitate was filtered, and washed with water and methanol to give 3.32 grams of solid product melting at 194°–196°C. Recrystallization from methyl cellosolve gave 3.1 grams of N-(3-methoxy-2-naphthoyl)-N'-(2-naphthoyl)hydrazine (IXb) melting at 194°–196°C.

In a similar manner, ethyl 1-naphthoate can be used to prepare N-(3-methoxy-2-naphthoyl)-N'-(1-naphthoyl)hydrazine.

EXAMPLE 4

A plurality of samples were prepared for testing by the following procedure. In a pint jar, the appropriate additive or additive combination (as indicated in the following table) was dry-blended with 40 grams of a copolymer of ethylene and propylene wire and cable grade, melt-flow 4.0 (Hercules). The mixture was then milled on a two-roll plastic mill at 170°C. for 3 minutes. The milled polymer was then molded into a plurality of 18 ± 2 mil films at 210°C. by heating in a press for 3 minutes under 28-ton pressure. The films were then cooled by forced air. A 1⅛ inch square 16 mil thick piece of 60 mesh copper screen was cleaned by heating in trichloroethylene and air drying, after which it was placed between two pieces of polymer film previously prepared and compression molded at 210°C. for 1.5 minutes to form a laminate at least 26–28 mils thick. The laminate was aged in forced draft oven at 140°C. and the efficiencies of the various additives were measured in terms of the time (in hours) for the polymer to become embrittled. The results obtained were:

| Copper Inhibitor | Oven Aging at 140°C Hours to Embrittlement |
| --- | --- |
| None | 7** |
| None | 170*** |
| Product(IXa) of Ex.2 | <8**** |
| Product (IXb) of Ex. 3 | <8**** |
| Product (IXa) of Ex. 2 | 1900–1917* |
| Product (IXb) of Ex. 3 | 1420–1437* |

Notes:
*The copper inhibitors, were used at a concentration of 0.2% in combination with 0.2% pentaerythrityl tetrakis-3-(3,5-di-t-butyl-4-hydroxy-phenyl)propionate, a hindered-phenol antioxidant.
**No copper inhibitor and no antioxidant used.
***0.2% antioxidant only, no copper inhibitor used.
****0.2% copper inhibitor only, no antioxidant used.

It is clear from the data in the foregoing table that (a) these copper inhibitors have no significant stabilizing properties against copper-catalyzed thermal degradation of polypropylene when used alone, (b) the conventional hindered-phenol antioxidant, provides poor stabilization against copper-catalyzed thermal degradation of polypropylene when used alone, and (c) the combinations of these copper inhibitors with the conventional hindered-phenol antioxidant provide a very high level of protection against copper-catalyzed thermal degradation of polypropylene.

What is claimed is:

1. A stabilizer composition useful in the enhancement of the resistance of polyolefins to copper-catalyzed thermal degradation comprising, in combination, a hindered-phenol antioxidant and a compound of the formula

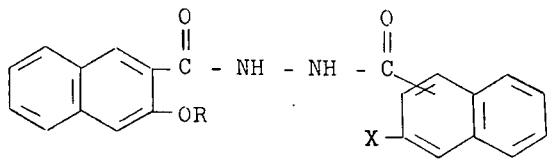

wherein R is alkyl of 1 to 8 carbon atoms, and X is hydrogen or —OR.

2. A composition as defined in claim 1 wherein R is methyl and X is hydrogen or methoxy.

3. A composition as defined in claim 2 wherein X is methoxy.

4. A composition as defined in claim 1 wherein said hindered-phenol antioxidant is pentaerythrityl tetrakis-3-(3,5-di-t-butyl-4-hydroxyphenyl)propionate.

5. A composition comprising a polyolefin and a stabilizing amount of the stabilizer composition of claim 1.

6. A composition as defined in claim 5 wherein said polyolefin is polypropylene.

7. A composition comprising a polyolefin and a stabilizing amount of the stabilizing composition of claim 2.

8. A composition comprising a polyolefin and a stabilizing amount of the stabilizing composition of claim 3.

9. Polypropylene stabilized against copper-catalyzed thermal degradation by the combination of (a) an amount of a hindered-phenol antioxidant sufficient to stabilize said polypropylene against thermal degradation in the absence of copper and (b) an amount of a compound of claim 1 sufficient to reduce the effects of copper on such thermal degradation even in the presence of said hindered-phenol antioxidant.

10. A composition as defined in claim 9 wherein said compound has the formula

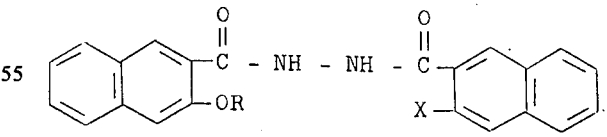

11. A composition as defined in claim 10 wherein R is methyl and X is hydrogen or methoxy.

12. A composition as defined in claim 11 wherein X is methoxy.

13. A composition as defined in claim 9 wherein said hindered phenol antioxidant is pentaerythrityl tetrakis-3-(3,5-di-t-butyl-4-hydroxyphenyl)propionate.

* * * * *